US009499582B2

(12) United States Patent
Mograbi

(10) Patent No.: US 9,499,582 B2
(45) Date of Patent: Nov. 22, 2016

(54) COMPOSITIONS AND METHODS FOR INCREASING CARNITINE LEVEL IN MUSCLE TISSUE

(71) Applicant: Oneday—Biotech And Pharma Ltd., Tel Aviv (IL)

(72) Inventor: Josef Mograbi, Tel Aviv (IL)

(73) Assignee: GENESISTEC LTD., Katzrin (IL)

( * ) Notice: Subject to any disclaimer, the term of this patent is extended or adjusted under 35 U.S.C. 154(b) by 0 days.

(21) Appl. No.: 14/603,792

(22) Filed: Jan. 23, 2015

(65) Prior Publication Data

US 2015/0133394 A1  May 14, 2015

Related U.S. Application Data

(63) Continuation of application No. PCT/IL2013/050632, filed on Jul. 24, 2013.

(60) Provisional application No. 61/675,350, filed on Jul. 25, 2012.

(51) Int. Cl.
A61K 38/07 (2006.01)
A61K 38/08 (2006.01)
C07K 5/103 (2006.01)
A61K 31/205 (2006.01)
A61K 31/375 (2006.01)
A23L 1/305 (2006.01)

(52) U.S. Cl.
CPC ............ *C07K 5/1013* (2013.01); *A23L 1/3053* (2013.01); *A61K 31/205* (2013.01); *A61K 31/375* (2013.01); *A61K 38/07* (2013.01); *A61K 38/08* (2013.01); *A23V 2002/00* (2013.01)

(58) Field of Classification Search
CPC ........... A61K 2300/00; A61K 31/205; A61K 31/375; A61K 38/07; A61K 38/08; A23L 1/3053; A23V 2002/00; C07K 5/1013
USPC ...................................................... 514/21.9
See application file for complete search history.

(56) References Cited

U.S. PATENT DOCUMENTS

| 4,966,848 | A |   | 10/1990 | Smith et al. |
| 5,223,421 | A |   | 6/1993 | Smith et al. |
| 5,837,218 | A |   | 11/1998 | Peers et al. |
| 5,874,468 | A |   | 2/1999 | Atlas et al. |
| 5,889,055 | A | * | 3/1999 | Howard ................ A61K 31/22 514/561 |
| 5,928,926 | A |   | 7/1999 | Kurdi-Haidar et al. |
| 5,985,261 | A |   | 11/1999 | White et al. |
| 6,369,106 | B1 |  | 4/2002 | Atlas et al. |
| 6,627,746 | B1 |  | 9/2003 | Doberstein et al. |
| 6,903,136 | B2 |  | 6/2005 | Miller et al. |
| 7,195,766 | B2 |  | 3/2007 | White |
| 7,307,063 | B2 |  | 12/2007 | Sharma et al. |
| 7,534,438 | B2 |  | 5/2009 | White |
| 8,735,343 | B2 |  | 5/2014 | White |
| 8,802,635 | B2 | * | 8/2014 | Mograbi ............. C07K 5/0202 514/15.1 |
| 9,034,824 | B2 | * | 5/2015 | Mograbi ............. C07K 5/0202 514/1.9 |
| 2006/0057188 | A1 |  | 3/2006 | Gaetani |
| 2007/0033666 | A1 |  | 2/2007 | Harris et al. |
| 2008/0009448 | A1 |  | 1/2008 | Sakurada |
| 2008/0069839 | A1 |  | 3/2008 | Guan et al. |
| 2009/0156508 | A1 |  | 6/2009 | Schteingart et al. |
| 2009/0285912 | A1 |  | 11/2009 | Rodriquez |
| 2011/0318380 | A1 |  | 12/2011 | Brix et al. |
| 2015/0218211 | A1 | * | 8/2015 | Mograbi ............. C07K 5/0202 514/1.9 |

FOREIGN PATENT DOCUMENTS

| WO | 9533765 A1 | 12/1995 |
| WO | 99/62927 A1 | 12/1999 |
| WO | 0234202 A2 | 5/2002 |
| WO | 02099084 A2 | 12/2002 |
| WO | 2004024868 A2 | 3/2004 |
| WO | 2004111636 A2 | 12/2004 |
| WO | 2005075679 A2 | 8/2005 |
| WO | 2005123108 A2 | 12/2005 |
| WO | 2010037395 A2 | 4/2010 |
| WO | 2012098546 A2 | 7/2012 |
| WO | 2014016831 A1 | 1/2014 |

OTHER PUBLICATIONS

Vitamin C from http://www.globalhealingcenter.com/natural-health/foods-high-in-vitamin-c/, pp. 1-3. Accessed Feb. 1, 2016.*
Bachnoff et al., (2011) Alleviation of oxidative stress by potent and selective thioredoxin-mimetic peptides. Free Radic Biol Med 50(10): 1355-67.
Bartov et al., (2006) Low molecular weight thiol amides attenuate MAPK activity and protect primary neurons from Aβ (1-42) toxicity. Brain Res 1069(1): 198-206.
Behrends et al., (1996) Evaluation of the secondary structure of vaccinia-virus thymidine kinase by circular-dichroism spectroscopy of overlapping synthetic peptides. Eur J Biochem 241(1): 126-132.
Calvani et al., (2003) The role of carnitine system in maintaining muscle homeostasis. Basic Appl Myol 13(3): 105-120.
Clay et al., (2001) Mitochondrial disease: a pulmonary and critical-care medicine perspective. Chest 120(2): 634-48.
Flanagan et al., (2010) Role of carnitine in disease. Nutr Metab (Lond) 7:30.
Grinberg et al., (2005) N-acetylcysteine amide, a novel cell-permeating thiol, restores cellular glutathione and protects human red blood cells from oxidative stress. Free Radic Biol Med 38(1): 136-145.

(Continued)

*Primary Examiner* — Julie Ha
(74) *Attorney, Agent, or Firm* — Vorys, Sater, Seymour & Pease LLP

(57) ABSTRACT

Compositions and methods utilizing thiol-containing short peptides having the sequence Cys-Lys-Met-Cys (SEQ ID NO: 1) and optionally N- and C-terminal modifications are described, for increasing carnitine level in muscle tissues, and treating or preventing diseases or disorders affecting muscle tissue.

16 Claims, 1 Drawing Sheet

(56) References Cited

OTHER PUBLICATIONS

Hiatt et al., (1989) Carnitine and acylcarnitine metabolism during exercise in humans. Dependence on skeletal muscle metabolic state. J Clin Invest 84(4): 1167-1173.
Kim et al., (2011) A novel dithiol amide CB3 attenuates allergic airway disease through negative regulation of p38 mitogen-activated protein kinase. Am J Respir Crit Care Med 183(8):1015-1024.
Krajcovicová-Kudláčková et al., (2000) Correlation of carnitine levels to methionine and lysine intake. Physiol Res 49(3): 399-402.
Liang and Nishino (2010) State of the art in muscle lipid diseases. Acta Myol 29(2):351-6.
Liang and Nishino (2011) Lipid storage myopathy. Curr Neurol Neurosci Rep 11(1): 97-103.
Muscular dystrophy association (MDA) Inc.,"Facts About Mitochondrial Myopathies", updated Dec. 2009.
Terrill et al., (2011) N-Acetylcysteine treatment of dystrophic mdx mice results in protein thiol modifications and inhibition of exercise induced myofibre necrosis. Neuromuscul Disord 22(5): 427-34.
Tiwari et al., (2009) Radiation-induced micronucleus formation and DNA damage in human lymphocytes and their prevention by antioxidant thiols. Mutat Res 676(1-2): 62-68.
Vaz and Wanders (2002) Carnitine biosynthesis in mammals. Biochem J 361(Pt 3): 417-29.
J. Amer, et al. "Red blood cells, platelets and polymorphonuclear neutriphils of patients with sickle cell disease exhibit oxidative stress that can be ameliorated by antioxidants" Blackwell Publishing Ltd, British Journal of Haematology; 2005,vol. 132; pp. 108-113.
J. Amer, at al. "N-acetylcysteine amide AD4 attenuates oxidative stress in beta-thalassemia blood cells" Biochimica et Biophysica Acta 1780; 2008, pp. 249-255.
N. Ballatori, et al. "Glutathione dysregulation and the etiology and progression of human diseases" Biol. Chem., vol. 390, pp. 191-214, Mar. 2009; pp. 191-214.
S. Banerjee; "Hemolytic Uremic Syndrome" Indian Pediatrics, vol. 46—Dec. 2009; pp. 1075-1084.
W. Breuer, et al; "Non-transferrin bound iron in Thalassemia—differential detection of redox active forms in children and older patients" American Journal of Hematology; Wiley Periodicals, Inc; <http://wileyonlinelibrary.com/cgi-bin/jhome/35105>;2011; pp. 55-61.
I. Cacciatore, et al; "Prodrug Approach for Increasing Cellular Glutathione Levels" Molecules; ISSN 1420-3049;<www.mdpi.com/journal/molecules> 2010; pp. 1242-1264.
C. Chassaing, et al.; "Determination of Reduced and Oxidized homocystein and related thiols in plasma by thiol-specific pre-column derivatization and capillary electrophoresis with laser-induced fluorescence detection" Journal of Chromatography B, 735; 1999; pp. 219-227.
E. Fibach; "Techniques for Studying Stimulation of Fetal Hemoglobin Production in Human Erythroid Cultures" Hemoglobin, 22, vol. 5 and 6; 1998; pp. 445-458.

E. Fibach, et al.; "The Role of Oxidative Stress in Hemolytic Anemia" Current Molecular Medicine, vol. 8; 2008; pp. 609-619.
E. Fibach, et al; "Amelioration of Oxidative Stress in Red Blood Cells from Patients with B-thalassemia Major and Intermedia and E-B-thalassemia Following Administration of a Fermented Papaya Preparation" Phytotherapy Research, vol. 24; 2010; pp. 1334-1338.
A. Fraternale, et al.; "GSH and Analogs in antiviral therapy" Molecular Aspects of Medicine, vol. 30; 2009; pp. 99-110.
P. Gallagher; "Hereditary Elliptocytosis—Spectrin and Protein" Seminars in Hematology, vol. 41, No. 2; Apr. 2004; pp. 142-164.
B. Gehrs, et al.; "Autoimmune Hemolytic Anemia" American Journal of Hematology, vol. 69; 2002; pp. 258-271.
J.R. Hess; "An update on solutions for red cell storage" Von Sanguinis, vol. 91; Blackwell Publishing; 2006; pp. 13-19.
V. Hudson; "Rethhinking Cystic Fibrosis Pathology—The Crical Role of Abnormal Reduced Glutathione (GSH) Transport Caused by CTFR Mutation" Free Radical Biology & Medicine, vol. 30, No. 12; Elsevier Science, Inc; 2001; pp. 1440-1461.
E. Kohne; "Hemoglobinopathies—Clinical Manifestations Diagnosis and Treatment" Deutsches Arzteblatt International; Dtsch Arztebl Int, vol. 108, No. 31-32; 2011; pp. 532-540.
A. Koren, et al.; "Response to Hydroxyyurea therapy in B-thalassemia" American Journal of Hematology;<www3.interscience.wiley.com/cgi-bin/jhome/35105>; Wiley-Liss, Inc; 2008; pp. 366-370.
M. Yan, et al.; "Endoplasmic Reticulum Stress" Neoplasia Press, Inc, vol. 10, No. 2; <www.neoplasia.com>; Feb. 2008; pp. 160-167.
J. Owen, et al.; "Measurement of Oxidized-Reduced Glutathione Ratio" Protein Misfolding and Cellular Stress in Disease and Aging-Concepts and Protocols, Methods in Molecular Biology, vol. 648; Springer Science Business Media, LLC; 2010; pp. 269-277.
D. Townsend, et al.; "Dossier—Oxidative stress pathologies and antioxidants—The importance of glutathione in human disease" Biomedicine & Pharmacotherapy, vol. 57; 2003; pp. 145-155.
L. Withers, et al.; "Proline—A Novel Cryoprotectant for the Freeze Preservation of Cuktured Cells of *Zea mays* L" Plant Physiol, vol. 64; 1979; pp. 675-678.
G. Wu, et al.; "Recent Advances in Nutritional Sciences—Glutathione Metabolism and Its Implications for Health" American Society for Nutritional Sciences; Dec. 2003; pp. 489-492.
Batt et al. (2010) The Hospital Physician® Board Review Manuals, Hematology, vol. 5, Part 3 pp. 1-12, Hemoglobinopathies, published by Turner White Communications, Inc.
Bolton-Maggs et al., (2004) Guidelines for the diagnosis and management of hereditary spherocytosis. Br J Haematol 126(4): 455-474.
Lu et al., (2009) Regulation of glutathione synthesis. Mol Aspects Med 30(1-2): 42-59.
N-acetylcysteine from http://www.naturalremedies.org/n-acetylcysteine!, pp. 1-6, accessed Feb. 1, 2016.
A0A078CKJ2 from UniProt, pp. 1-3. Sequence updated on Oct. 29, 2014. Accessed Mar. 26, 2016.
Q85485 from UniProt, pp. 1-3. Sequence updated on Nov. 1, 1996. Accessed Mar. 26, 2016.

\* cited by examiner

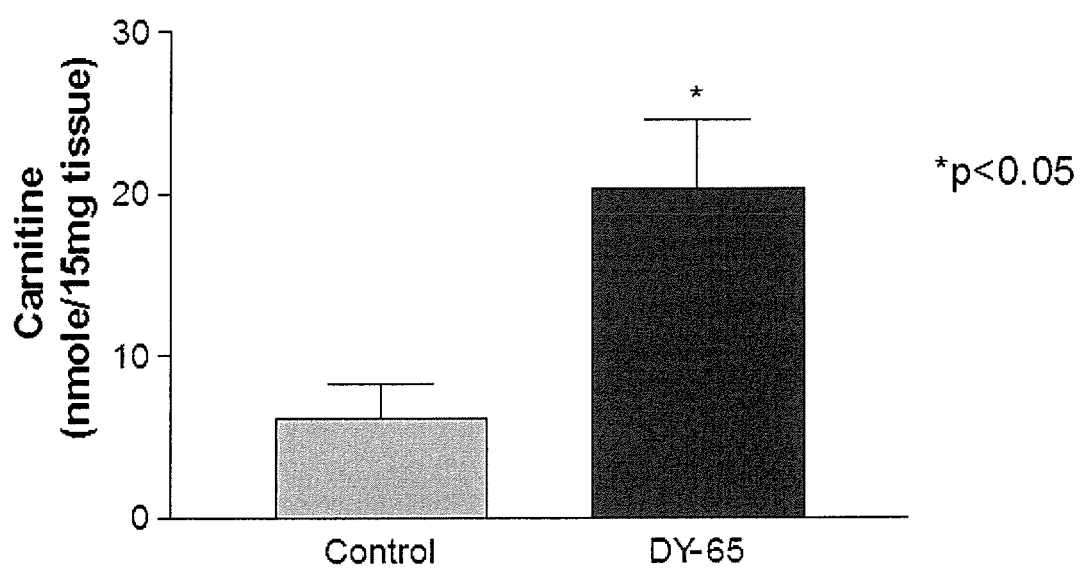

COMPOSITIONS AND METHODS FOR INCREASING CARNITINE LEVEL IN MUSCLE TISSUE

FIELD OF THE INVENTION

The present invention relates to compositions and methods for increasing carnitine level in tissues. More specifically, the present invention relates to compositions comprising short thiol-containing peptides, and uses thereof for increasing the level of carnitine in muscle tissue and treating diseases affecting muscle tissue.

BACKGROUND OF THE INVENTION

L-carnitine (3-hydroxy-4-N-trimethylamino-butyrate), the biologically active and naturally occurring form of carnitine, is a quaternary amine that is required in energy metabolism in mammals. Carnitine is a water soluble organic compatible solute with various biological functions, mainly as a carrier of acyl moieties, such as long chain fatty acids. Carnitine is required for the transport of fatty acids from the cytosol into the mitochondria for beta-oxidation during the breakdown of lipids for the generation of metabolic energy. Carnitine is also known to have antioxidant activity.

To exert its metabolic function, carnitine forms esters with a wide range of fatty acyl groups (i.e. acylcarnitines), a reaction mediated by an enzyme localized to the outer mitochondrial membrane, known as carnitine acyltransferase (e.g. carnitine palmitoyltransferase). The resulting acylcarnitine esters can be transported over the inner mitochondrial membrane into the mitochondrial matrix, where carnitine is separated from the fatty acid chain. The fatty acid proceeds to oxidation, while the free carnitine can be transported back out of the mitochondria to allow the transfer process to continue.

In humans, carnitine may be obtained from food or by endogenous biosynthesis. L-carnitine is biosynthesized primarily in the liver and kidneys from the amino acids lysine (via trimethyllysine) and methionine. Lysine provides the carbon backbone of carnitine while the 4-N-methyl groups originate from methionine. Krajcovicová-Kudláčková et al. have studied the correlation between lysine and methionine intake, and the plasma level of carnitine (Krajcovicová-Kudláčková et al., *Physiol Res.* 2000; 49(3):399-402).

Vitamin C (also known as ascorbic acid) is essential to the synthesis of carnitine, as it is required for the enzymatic activity of trimethyl-lysine (TML) dioxygenase, the first enzyme in the carnitine synthesis chain. Oxidized vitamin C can be reduced back to its un-oxidized (reduced) state via, inter alia, elevating cysteine levels.

Carnitine molecules, either exogenously-consumed or endogenously-synthesized, enter cells via special transporters. Carnitine molecules are found mainly in brain, heart, muscles, nerve tissue and sperm.

Because of its central role in transporting fatty acids to the site of oxidation, adequate levels of carnitine are required for normal fatty acid and energy metabolism in tissues.

Sufficient levels of carnitine are particularly important in body parts that require high energy and utilize fatty acids as an energy source, such as muscles.

Carnitine is commercially available as a nutritional supplement. Carnitine is also available as a prescription drug for injection or oral administration, for example CARNITOR® and LEVOCARNITINE™, which are indicated for the treatment of primary systemic carnitine deficiency, and for acute and chronic treatment of patients with an inborn error of metabolism which results in secondary carnitine deficiency. Carnitine supplementation is used in some medical conditions, such as mitochondrial diseases, including mitochondrial myopathies, and neuromuscular disorders. It is sometimes used by athletes in order to improve performance.

Thiol (—SH) containing compounds are a type of molecules capable of neutralizing several types of damaging oxidative species, thus acting as reducing reagents. The activity of this group of compounds is mainly due to the sulfur atom they comprise which participates in nucleophilic attack on toxic electrophiles, scavenging free radicals, effecting repair of damaged targets through hydrogen atom donation, altering the redox status of the cell, or affecting gene transcription or protein function.

WO 2002/034202 discloses an antioxidant compound characterized by (a) a peptide including at least three amino acid residues of which at least two are cysteine residues, each having a readily oxidizable sulfhydryl group for effecting antioxidation; and at least two peptide bonds, each being cleavable by at least one intracellular peptidase; and (b) a first hydrophobic or non-charged moiety being attached to an amino terminal of the peptide via a first bond and a second hydrophobic or non-charged moiety being attached to a carboxy terminal of the peptide via a second bond, the first hydrophobic or non-charged moiety and the second hydrophobic or non-charged moiety are selected so as to provide the antioxidant compound with membrane miscibility properties for permitting the antioxidant compound to cross cellular membranes; wherein cleavage of the at least two peptide bonds by the at least one intracellular peptidase results in generation of a plurality of antioxidant species, each including one of the cysteine residues having the readily oxidizable sulfhydryl group and which is also active in effecting antioxidation, thereby providing for a plurality of different antioxidant species acting in synergy in exerting antioxidation.

WO 2012/098546, to the inventor of the present invention and others, published after the priority date of the present application, discloses potent compounds having combined antioxidant, anti-inflammatory, anti-radiation and metal chelating properties. Short peptides having said properties and methods and uses of such short peptides in clinical and cosmetic applications are disclosed. Among other peptides, Cys-Lys-Met-Cys (SEQ ID NO: 1) and Cys-Met-Lys-Cys (SEQ ID NO: 2) are disclosed.

Effective compositions and methods for increasing carnitine level in tissues, particularly muscle tissue, are desired.

SUMMARY OF THE INVENTION

The present invention provides compositions comprising synthetic short thiol-containing peptides for use in increasing carnitine levels in muscle tissues effectively and specifically. The compositions of the present invention may be formulated, in some embodiments, as pharmaceutical compositions or dietary supplements. The compositions of the invention may be formulated in some embodiments together with additional active agents. According to some particular embodiments, the compositions further comprise vitamin C or a salt thereof.

The present invention further provides methods for increasing the level of carnitine in muscle tissue, and methods for treating diseases or disorders affecting muscle tissue, utilizing the above compositions.

The highly potent peptide compounds utilized herein comprise the dipeptide sequence lysine-methionine flanked by two cysteine residues, namely Cys-Lys-Met-Cys (SEQ ID NO: 1), and optionally further comprise N- and C-terminal modifications, such as N- and C-terminal blocking groups.

The present invention is based in part on the finding that administration of a peptide according to embodiments of the present invention to mice resulted in a significant and specific elevation of carnitine level in skeletal muscle tissue of the mice compared to baseline levels, as exemplified herein below. Surprisingly, other tissues, including liver and kidneys which are known to be the main sites of L-carnitine biosynthesis, did not demonstrate a significant elevation in carnitine level after the same treatment with the peptide. Unexpectedly, a closely-related peptide comprising a reverse order of the methionine and lysine (Cys-Met-Lys-Cys, SEQ ID NO: 2) did not show a similar effect. The peptides according to embodiments of the present invention are particularly beneficial for conditions where an increased carnitine level in muscles is desired.

Advantageously, administration of the peptides as disclosed herein results in higher levels of carnitine within muscle cells compared to direct administration of carnitine molecules. The elevation in carnitine level in skeletal muscle cells is thought to improve at least some of the clinical manifestations of the diseases and disorders specified herein. Elevated carnitine level in skeletal muscle cells is also thought to improve energy metabolism within these cells, which may be particularly beneficial for individuals who participate in sports, for example, during exercise.

According to one aspect, the present invention provides a method for increasing the level of carnitine in a skeletal muscle tissue of a subject, the method comprising administering to the subject a composition comprising as an active ingredient a peptide or a salt thereof having the amino acid sequence Cys-Lys-Met-Cys (SEQ ID NO: 1). According to preferred embodiments of the invention the level of carnitine in the skeletal muscle is significantly elevated without elevation of the carnitine levels in certain nonskeletal muscle tissues.

According to another aspect, the present invention provides a composition comprising as an active ingredient a peptide or a salt thereof having the amino acid sequence Cys-Lys-Met-Cys (SEQ ID NO: 1), for use in increasing the level of carnitine in skeletal muscles tissue.

In some embodiments, the peptide is of 4-10 amino acids.

In some embodiments, the administered composition is a pharmaceutical composition. In alternative embodiments, the composition is a dietary supplement. In additional embodiments, the composition is a medical food.

In some embodiments, the method is used for treating a disease or disorder affecting skeletal muscle tissue.

According to another aspect, the present invention provides a method for treating a disease or disorder affecting any skeletal muscle tissue in a subject in need thereof, the method comprising administering to the subject a pharmaceutical composition comprising as an active ingredient a peptide or a salt thereof having the amino acid sequence Cys-Lys-Met-Cys (SEQ ID NO: 1).

According to yet another aspect, the present invention provides a pharmaceutical composition comprising as an active ingredient a peptide or a salt thereof having the amino acid sequence Cys-Lys-Met-Cys (SEQ ID NO: 1), for use in the treatment of a disease or disorder affecting any skeletal muscle tissue.

In some embodiments, the disease or disorder is selected from the group consisting of carnitine deficiency (primary or secondary, muscle-restricted or systemic), a mitochondrial myopathy, a metabolic myopathy and a neuromuscular disease. Each possibility represents a separate embodiment of the present invention.

In some embodiments, the mitochondrial myopathy is selected from the group consisting of Kearns-Sayre syndrome, myoclonus epilepsy with ragged red fibers (MERRF), mitochondrial encephalomyopathy, lactic acidosis and stroke-like episodes (MELAS), Leigh syndrome, mitochondrial DNA depletion syndrome (MDS), neuropathy, ataxia and retinitis pigmentosa (NARP) and Pearson syndrome. Each possibility represents a separate embodiment of the present invention.

In some embodiments, the metabolic myopathy is a lipid storage disease.

In some embodiments, the lipid storage disease is selected from the group consisting of carnitine palmitoyltransferase (CPT) deficiency (including both CPT I and CPT II), carnitine/acylcarnitine translocase deficiency, very long-chain acylCoA dehydrogenase (VLCAD) deficiency, long-chain 3-hydroxyacyl-CoA dehydrogenase (LCHAD) deficiency, mitochondrial trifunctional protein (TFP) deficiency, medium-chain acylCoA dehydrogenase (MCAD) deficiency and glutaric aciduria type II. Each possibility represents a separate embodiment of the present invention.

In some embodiments, the neuromuscular disease is selected from the group consisting of muscular dystrophy, myotonic dystrophy, myasthenia gravis and amyotrophic lateral sclerosis (ALS). Each possibility represents a separate embodiment of the present invention.

In some embodiments, the methods of the present invention further comprise administering an additional active agent. In some embodiments, the additional active agent is vitamin C or a salt thereof.

In some embodiments, the vitamin C or salt thereof and the peptide or salt thereof are administered sequentially. In other embodiments, the vitamin C or salt thereof and the peptide or salt thereof are administered concurrently.

In some embodiments, the vitamin C or salt thereof and the peptide or salt thereof are within a single composition. According to these embodiments, the administered composition further comprises vitamin C or a salt thereof. In other embodiments, the vitamin C or salt thereof and the peptide or salt thereof are within separate compositions.

In some embodiments, the additional active agent is L-carnitine.

In some embodiments, carnitine and the peptide or salt thereof are administered sequentially. In other embodiments, carnitine and the peptide or salt thereof are administered concurrently. In some embodiments, carnitine and the peptide or salt thereof are within a single composition. According to these embodiments, the administered composition further comprises carnitine. In other embodiments, carnitine and the peptide or salt thereof are within separate compositions.

According to a further aspect, the present invention provides a composition comprising as active ingredients:
  (a) a peptide or a salt thereof having the amino acid sequence Cys-Lys-Met-Cys (SEQ ID NO: 1), and
  (b) an additional active agent or a salt thereof selected from the group consisting of vitamin C and L-carnitine.

In some embodiments, the composition is effective in increasing the level of carnitine in skeletal muscle tissue.

In some embodiments, the vitamin C is selected from the group consisting of ascorbic acid, calcium ascorbate, sodium ascorbate, ascorbyl palmitate, niacinamide ascorbate, manganese ascorbate, chromium ascorbate, molybdenum ascorbate, zinc ascorbate, magnesium ascorbate, and potassium ascorbate or any other mineral ascorbates. Each possibility represents a separate embodiment of the present invention.

In some embodiments, the carnitine is selected from the group consisting of L-carnitine, levocarnitine, acetylcarnitine, carnitine fumarate, carnitine arginate, carnitine taurinate and glycine propionyl-1-carnitine.

In some embodiments, the composition is formulated as a pharmaceutical composition. In other embodiments, the composition is formulated as a dietary supplement. In additional embodiments, the composition is formulated as a medical food.

In some embodiments, the peptide present in the compositions of the present invention further comprises at least one modification. According to some embodiments, the peptide comprises an amino-terminal modification. According to other embodiments, the peptide comprises a carboxy-terminal modification. According to yet other embodiments, the peptide comprises both amino-terminal and carboxy-terminal modifications. Each possibility represents a separate embodiment of the invention.

In principle, any pharmaceutically acceptable group suitable for amino terminus modification, and any pharmaceutically acceptable group suitable for carboxy terminus modification may be used for the peptide used according to embodiments of the present invention.

In some embodiments, the amino terminal modification is an amino terminal blocking group.

In some embodiments, the amino-terminal blocking group is selected from the group consisting of alkyl and acyl. Each possibility represents a separate embodiment of the invention.

In some exemplary embodiments, the amino-terminal blocking group is an acetyl group.

In some embodiments, the amino terminal modification is a cell penetration-enhancing moiety, which improves the ability of the peptide to penetrate lipid layers and/or improves the ability of the peptide to penetrate into the skin. In some exemplary embodiments, the moiety that improves that ability of the peptide to penetrate lipid layers and/or improves its ability to penetrate the skin is a fatty acid. In some embodiments, the fatty acid is selected from the group consisting of palmitic acid, phosphatidic acid, stearic acid, arachidonic acid, docosahexaenoic acid, eicosapentaenoic acid, and oleic acid. Each possibility represents a separate embodiment of the invention.

In some embodiments, the amino terminal modification is selected from the group consisting of an amino terminal blocking group and a fatty acid. Each possibility represents a separate embodiment of the invention.

In some embodiments, the amino terminal modification is selected from the group consisting of alkyl, acyl and a fatty acid.

In some embodiments, the carboxy-terminal modification is a carboxy terminal blocking group. In some embodiments, the carboxy terminal blocking group is selected from the group consisting of: amide, ester and alcohol group. In some exemplary embodiments, the carboxy terminal blocking group is an amide group.

In some embodiments, the peptide is cleavable by intracellular peptidases.

In some additional or alternative embodiments, the N- and/or C-terminal modifications are hydrolysable by intracellular enzymes. Thus, these modifications may be hydrolyzed upon entry of the peptide into cells.

In some specific exemplary embodiments, the compositions of the present invention comprise the peptide N-acetyl-Cys-Lys-Met-Cys-amide (SEQ ID NO: 3).

In some embodiments, the peptide is in the form of a pharmaceutically acceptable salt. In some embodiments, the pharmaceutically acceptable salt is selected from the group consisting of acetate and citrate salts. Each possibility represents a separate embodiment of the invention.

The compositions of the present invention may be administered by local and systemic routes.

In some embodiments, the compositions are formulated for local administration. In other embodiments, the compositions are formulated for systemic administration.

These and further aspects and features of the present invention will become apparent from the detailed description, examples and claims which follow.

BRIEF DESCRIPTION OF THE FIGURES

FIG. 1. Effect of N-acetyl-Cys-Lys-Met-Cys-$NH_2$ (SEQ ID NO: 3) on carnitine levels (carnitine concentrations) in mouse muscles.

DETAILED DESCRIPTION OF THE INVENTION

The present invention relates to the use of thiol-containing peptides for increasing the level of carnitine in muscle tissues, and treating and/or preventing disorders and medical conditions affecting muscle tissue.

Definitions

As used herein "peptide" indicates a sequence of amino acids linked by peptide bonds. In some embodiments, a peptide is composed of 10 amino acids or less, 9 amino acids or less, 8 amino acids or less, 7 amino acids or less, 6 amino acids or less, 5 amino acids or less, or 4 amino acids. In some embodiments, the peptide is composed of 4-10 amino acids, 4-9 amino acids, 4-8 amino acids, 4-7 amino acids, 4-6 amino acids, 4-5 amino acids, or 4 amino acids. Each possibility represents a separate embodiment of the invention. In some embodiments, a tetra-peptide is provided. The term "tetra-peptide" indicates a peptide composed of four amino acids. The peptides of the present invention are typically utilized in a linear form, although it will be appreciated that in cases where cyclization does not severely interfere with peptide characteristics, cyclic forms of the peptide can also be utilized.

The term "amino acid" refers to compounds, which have an amino group and a carboxylic acid group, preferably in a 1,2- 1,3-, or 1,4-substitution pattern on a carbon backbone. The term encompasses natural, non-natural and/or chemically modified amino acid residues. Natural amino acids include those found in proteins, which are L-amino acids. Non-natural and/or chemically modified amino acids include, for example, the corresponding N-methyl amino acids, side chain modified amino acids and the biosynthetically available amino acids which are not found in proteins (e.g., 5-hydroxy-lysine). The amino acid residues are represented throughout the specification and claims by either one or three-letter codes, as is commonly known in the art. The amino acids used in this invention are those which are available commercially or are available by routine synthetic methods. Certain residues may require special methods for incorporation into the peptide, and either sequential, divergent or convergent synthetic approaches to the peptide sequence are useful in this invention.

Also included within the scope of the invention are salts of the peptides, and derivatives of the peptides of the invention.

As used herein the term "salts", when referring to a peptide, refers to salts of carboxyl groups and to acid addition salts of amino groups of the peptide molecule. Salts of carboxyl groups may be formed by means known in the art and include inorganic salts, for example sodium, calcium, ammonium, ferric or zinc salts, and the like, and salts with organic bases such as salts formed for example with amines such as triethanolamine, piperidine, procaine, and the like. Acid addition salts include, for example, salts with mineral acids such as acetic acid, citric acid or oxalic acid. Examples of pharmaceutically acceptable acid addition salts may be found for instance in P. H. Stahl and C. G. Wermuth, editors, Handbook of Pharmaceutical Salts: Properties, Selection and Use, Weinheim/Zürich:Wiley-VCH/VHCA, 2002.

Esters and amides of carboxy groups and acyl and alkyl derivatives of amino groups may be introduced into the molecule by reacting targeted amino acid residues of the peptide with an organic derivatizing agent that is capable of reacting with terminal residues. Preferred chemical derivatives include peptides that have been C-termini amidated or N-termini acetylated.

"Derivatives" of the peptides of the invention as used herein covers derivatives which may be prepared from the functional groups which occur as side chains on the residues or the N- or C-terminal groups, by means known in the art, and are included in the invention as long as they remain pharmaceutically/cosmetically acceptable, i.e., they do not destroy the activity of the peptide, do not confer toxic properties on compositions containing it and do not adversely affect the antigenic properties thereof. These derivatives may, for example, include aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or carbocyclic aroyl groups).

"Permeability" refers to the ability of an agent or substance to penetrate, pervade, or diffuse through a barrier, membrane, or a skin layer. A "cell permeability-enhancing", "cell penetration-enhancing" or "permeability-enhancing" moiety refers to any molecule known in the art which is able to facilitate or enhance penetration of molecules through membranes. Non-limitative examples include: hydrophobic moieties such as lipids, fatty acids, steroids and bulky aromatic or aliphatic compounds. The permeability-enhancing moiety may be connected to any position in the peptide moiety, directly or through a spacer, preferably to the amino or carboxy terminus of the peptide moiety.

As used herein, the term "skeletal muscle" has its art recognized meaning and refers to a striated muscle, normally having at least one attachment to the skeletal system, whose contraction and extension are under the control of the somatic nervous system (voluntarily controlled in normal conditions). Non-limiting examples of skeletal muscles include skeletal muscles of the lower body, such as the quadriceps, hamstrings and the gastrocnemius muscles, and skeletal muscles of the upper body, such as, triceps, biceps, the extensor and flexor carpi ulnaris, deltoids, trapezius and pectoralis.

As used herein, the term "disease or disorder affecting skeletal muscle tissue" refers to a disease or disorder where functioning of one or more skeletal muscles is impaired, typically characterized by or manifested by at least one of: dysfunction of muscle fibers, muscle weakness, muscle cramps, muscle stiffness, muscular dystrophy and muscle spasm. A disease or disorder affecting skeletal muscle tissue may also be referred to as a myopathy.

As used herein, "treating" and "treatment", refers to reduction, amelioration or even elimination of at least some of the symptoms associated with the relevant disorder. For example, treatment may include at least one of improving fatty acid oxidation in muscle tissue, decreasing lipid accumulation in muscle tissue, reducing fatigue, restoring normal muscle tone, improving muscle function, improving mitochondrial respiratory chain, improving lactate metabolism, reducing muscles' fatigue, improving muscles' contractile power, improving muscles' stamina, reducing myolysis, reducing muscle atrophy, slowing progression of a myopathy, slowing progression of a neuromuscular disease or disorder, reducing concentration of reactive oxygen species, promoting desired muscle hypertrophy, promoting normal mitochondrial function, improving immune system function.

The term "treatment" may also encompass prophylactic treatment, which may be applied to populations at risk of developing muscle diseases or disorders. For example, individuals known to carry a certain mutation that is associated with a particular disease.

As used herein, the terms "increasing" or "reducing", when referring to a level of a certain substance or to a measurable index, are intended to refer to an increase or reduction, respectively, compared to an initial level, prior to the administration/treatment with a peptide as described herein.

As used herein, the term "about", when referring to a measurable value such as an amount or size, is meant to encompass variations of +/−10%, more preferably +/−5%, even more preferably +/−1%, and still more preferably +/−0.1% from the specified value, as such variations are appropriate to achieve the intended purpose.

Peptides

The present invention utilizes peptides and/or salts thereof having the amino acid sequence Cys-Lys-Met-Cys (SEQ ID NO: 1).

It is understood that Cys represents the amino-acid cysteine; Lys represents the amino-acid lysine; Met represents the amino-acid methionine.

In some embodiments, the peptide further comprises at least one modification selected from the group consisting of an amino-terminal modification and a carboxy-terminal modification. According to these embodiments, the peptide has the sequence Z-Cys-Lys-Met-Cys-Y (SEQ ID NO: 5), wherein Z is absent or represents an amino terminal modification and Y is absent or represents a carboxy terminal modification.

In some embodiments, the N- and C-termini modifications reduce the polarity of the peptides of the present invention, thus facilitating the ability of these peptides to cross cell membranes, enter easily into cells and accumulate within the cells. In addition, modifications of the peptide termini may improve bio-stability, for example by blocking the action of peptidases.

The amino and carboxy termini modifications may be chosen from any amino and carboxy termini modifications conventionally used in the art of peptide chemistry, which will not adversely affect the activities of the peptide.

In some embodiments, the amino terminal modification comprises addition of an amino terminal blocking group.

Blocking of the N terminus may be performed, for example, by alkylation or acylation, using methods well known in the art. Non-limiting examples of suitable N-terminal blocking groups include $C_1$-$C_5$ branched or unbranched alkyl groups, acyl groups such as formyl and acetyl groups, and substituted forms thereof, such as the acetamidomethyl (Acm) group. Each possibility represents a separate embodiment of the invention.

In some embodiments, the amino terminal modification comprises covalently linking to the N-terminus of the peptide a moiety that improves the ability of the peptide to penetrate lipid layers and/or improves the ability of the peptide to penetrate into the skin. Such moiety may provide high efficacy topical administration. In some exemplary embodiments, the moiety is a fatty acid. The fatty acid may be selected from the group consisting of palmitic acid, phosphatidic acid, stearic acid, arachidonic acid, docosahexaenoic acid, eicosapentaenoic acid and oleic acid. Each possibility represents a separate embodiment of the invention.

In some typical embodiments, the amino terminal modification is selected from the group consisting of acetyl, alkyl, acyl and a fatty acid. Each possibility represents a separate embodiment of the invention.

In some embodiments, the carboxy terminal modification is a carboxy terminal blocking group.

Blocking of the C terminus may be performed, for example, by amidation, reduction or esterification, using methods well known in the art. Non-limiting examples of suitable C-terminal blocking groups include amide, ester, and alcohol groups. Each possibility represents a separate embodiment of the invention.

Upon entry of the peptides into cells they may undergo cleavage by intracellular peptidases.

In addition, the N- and/or C-termini modifications of the peptides may be hydrolyzed, which may result in their accumulation in the cytosol.

In some embodiments, the peptide is a tetra-peptide with the sequence Cys-Lys-Met-Cys (SEQ ID NO: 1).

In some exemplary embodiments, the peptide N-acetyl-Cys-Lys-Met-Cys-amide (SEQ ID NO: 3) is provided.

The peptides may be synthesized by any technique known to those skilled in the art of peptide synthesis. These methods include solid phase as well as solution phase synthesis methods.

Solid phase peptide synthesis procedures are well known in the art and further described by John Morrow Stewart and Janis Dillaha Young, Solid Phase Peptide Syntheses (2nd Ed., Pierce Chemical Company, 1984).

A skilled artesian may synthesize any of the peptides of the present invention by using an automated peptide synthesizer using standard chemistry such as, for example, t-Boc or Fmoc chemistry.

The methods include exclusive solid phase synthesis, partial solid phase synthesis methods, fragment condensation, classical solution synthesis.

Synthetic peptides can be purified by preparative high performance liquid chromatography (Creighton T. (1983) Proteins, structures and molecular principles. WH Freeman and Co. N.Y.) and the composition of which can be confirmed via amino acid sequencing. Some of the peptides of the invention, which include only natural amino acids, may further be prepared using recombinant DNA techniques known in the art. The conjugation of the peptidic and permeability moieties may be performed using any methods known in the art, either by solid phase or solution phase chemistry. Some of the compounds of the present invention may conveniently be prepared using solution phase synthesis methods. Other methods known in the art to prepare compounds like those of the present invention can be used and are comprised in the scope of the present invention.

The permeability-enhancing moiety of the present invention may be connected to any position in the peptide moiety, directly or through a spacer. According to a specific embodiment, the cell-permeability moiety is connected to the amino terminus of the peptide moiety. The optional connective spacer may be of varied lengths and conformations comprising any suitable chemistry including but not limited to amine, amide, carbamate, thioether, oxyether, sulfonamide bond and the like. Non-limiting examples for such spacers include amino acids, sulfone amide derivatives, amino thiol derivatives and amino alcohol derivatives.

Cyclic versions of the peptides disclosed herein are also within the scope of the present invention. Cyclization of peptides may take place by any means known in the art, for example through free amino and carboxylic groups present in the peptide sequence, or through amino acids or moieties added for cyclization. Non limiting examples of cyclization types are: side chain to side chain cyclization (e.g., through S—S bonds), C-to-N terminal cyclization, side chain to terminal cyclization, and any type of backbone cyclization incorporating at least one $N^{\alpha}$-ω-substituted amino acid residue/s as described for example in WO 95/33765.

Other methods known in the art to prepare peptides like those of the present invention can be used and are within the scope of the present invention.

In some embodiments, the peptide is in the form of a salt. Non-limiting examples of suitable salts include trifluoroacetic acid (TFA), acetate and citrate salts.

Compositions of the Present Invention

The present invention provides compositions comprising as an active ingredient a peptide or a salt thereof having the amino acid sequence Cys-Lys-Met-Cys (SEQ ID NO: 1).

The present invention further provides compositions comprising the peptide or salt thereof and vitamin C or a salt thereof as the active ingredients.

The present invention further provides compositions comprising the peptide or salt thereof and carnitine or salt thereof as the active ingredients.

This combination of active ingredients is contemplated to act at least additively and preferably synergistically to induce an increase in the level of carnitine within muscle cells.

Any form of vitamin C may be used, including for example ascorbic acid, calcium ascorbate, sodium ascorbate, ascorbyl palmitate, niacinamide ascorbate, manganese ascorbate, chromium ascorbate, molybdenum ascorbate, zinc ascorbate, magnesium ascorbate, potassium ascorbate or any other mineral ascorbates, or a combination thereof.

Carnitine (used herein interchangeably with "L-carnitine") is available in several forms. Examples of suitable forms of carnitine for use according to embodiments of the present invention include L-carnitine, levocarnitine, acetylcarnitine, carnitine fumarate, carnitine arginate, carnitine taurinate and glycine propionyl-1-carnitine.

The compositions of the present invention include pharmaceutical compositions, medical food and dietary supplements.

The term "pharmaceutical composition", as used herein, refers to a preparation comprising a therapeutically effective amount of active ingredients, to be administered to a subject in order to treat or prevent a certain medical condition. The active ingredients are present in the pharmaceutical composition in amount which is effective to achieve a desired therapeutic activity, as known in the art. Pharmaceutical compositions can be formulated for a variety of routes of administration, as will be explained in more detail below.

The term "dietary supplement", as used herein, refers to a preparation intended to supplement the diet and provide nutrients that may be missing or may not be consumed in sufficient quantities in a person's diet, or to provide an extra dose of certain nutrients that may be beneficial in certain conditions. In particular, dietary supplements according to embodiments of the present invention are intended to supplement the diet with carnitine or carnitine-elevating compound. Dietary supplements are typically formulated for oral consumption, for example, as pills, capsules, tablets, or liquid dosage forms.

The term "medical food", as used herein, refers to a food which is formulated to be consumed or administered enterally, usually under the supervision of a physician, and which is specially formulated and intended for the dietary management of a disorder that has distinctive nutritional needs that cannot be met well enough by a normal diet alone. In addition to the active ingredients, the medical food may further comprise a carrier material, such as oat meal gruel, lactic acid fermented foods, resistant starch, dietary fibers, carbohydrates, proteins and glycosylated proteins.

In some embodiments, a nutritional composition is provided, the composition comprises at least one of the above peptides and optionally any form of vitamin C, said composition is effective in increasing the level and/or concentration of carnitine molecules within skeletal muscle tissue.

The compositions of the present invention further include pharmaceutically acceptable diluents, excipients or carriers.

As used herein, the term "pharmaceutically acceptable diluent, excipient, or carrier" refers to a diluent, excipient, or carrier that does not cause significant irritation to an organism and does not abrogate the biological activity and properties of the administered active agent.

As used herein, the term "excipient" refers to an inert substance added to a composition to further facilitate administration of an active ingredient. Non-limiting examples of excipients include calcium carbonate, calcium phosphate, various sugars and types of starch, cellulose derivatives, gelatin, vegetable oils, and polyethylene glycols. Techniques for formulation and administration of drugs may be found in "Remington's Pharmaceutical Sciences", Mack Publishing Co., Easton, Pa., (Remington: The Science and Practice of Pharmacy, Gennaro, A., Lippincott, Williams & Wilkins, Philadelphia, Pa., 20th ed, 2000).

As used herein, a "carrier" refers to any substance suitable as a vehicle for delivering of the agents or molecule of the present invention to a suitable in vivo or in vitro site. As such, carriers can act as a pharmaceutically acceptable excipient of a therapeutic composition of the present invention. Carriers of the present invention include: (1) excipients or formularies that transport, but do not specifically target a molecule to a cell (referred to herein as non-targeting carriers); and (2) excipients or formularies that deliver a molecule to a specific site in a subject or a specific cell (i.e., targeting carriers). Examples of non-targeting carriers include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

The compositions of the present invention can be sterilized by conventional methods.

In some embodiments, the compositions further comprise at least one more active ingredient.

In some embodiments, a composition is provided, consisting of the peptide of the present invention as an active ingredient.

The peptide of the present invention or a salt thereof, and optionally additional one or more active ingredients, are present in the compositions of the present invention in an amount effective to achieve the intended purpose, for example, in an amount effective to treat a certain disease.

The compositions of the present invention may be administered by local or systemic routes. Systemic administration includes enteral and parenteral routes. Non-limiting examples of suitable administration routes include topical application, oral, rectal, transmucosal such as transnasal and buccal, intravenous, intramuscular, transdermal, subcutaneous, intradermal, intravitreal, intravesicular and inhalation routes. Each possibility represents a separate embodiment of the present invention. The compositions of the present invention may be formulated for sustained release of the active ingredient.

Thus, in some embodiments, the compositions of the present invention are formulated for topical administration. In other embodiments, the compositions are formulated for systemic administration.

The compositions of the present invention may be formulated in conventional manners. The proper formulation is dependent upon the route of administration chosen.

In some embodiments, the compositions of the present invention are formulated for topical use. Non-limiting examples of formulations for topical use include cream, ointment, lotion, gel, foam, suspension, aqueous or cosolvent solutions, salve, liposome and sprayable liquid form. The composition may also form part of a patch for transdermal application. Other suitable topical product forms for the compositions of the present invention include, for example, emulsion, mousse, lip balm, lip gloss, lotion, mask, pomade, solution and serum.

In some embodiments, the compositions of the present invention are formulated for oral administration. For oral administration, enteric-coated preparations or dosage forms, microspheres, liposomes and nanoparticles for oral delivery of peptides and proteins may be used. Non-limiting examples of formulations for oral administration include tablets, pills, dragees, capsules, liquids, gels, syrups, slurries, suspensions, and the like, for oral ingestion by a patient. Suitable carriers for oral administration are well known in the art. Compositions for oral use can be made using a solid excipient, optionally grinding the resulting mixture, and processing the mixture of granules, after adding suitable auxiliaries as desired, to obtain tablets or dragee cores. Non-limiting examples of suitable excipients include fillers such as sugars, including lactose, sucrose, mannitol, or sorbitol, cellulose preparations such as, maize starch, wheat starch, rice starch, potato starch, gelatin, gum tragacanth, methyl cellulose, hydroxypropylmethyl-cellulose, and sodium carbomethylcellulose, and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

For administration by injection, the active ingredients of the composition may be formulated in aqueous solutions, for example in physiologically compatible buffers including but not limited to Hank's solution, Ringer's solution, or physiological salt buffer. Formulations for injection may be presented in unit dosage forms, for example, in ampoules, or in multi-dose containers with, optionally, an added preservative. The compositions may be in the form of suspensions, solutions, or emulsions in oily or aqueous vehicles, and may contain formulatory agents such as suspending, stabilizing, and/or dispersing agents. Non-limiting examples of suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions. Alternatively, the active ingredient may be in powder form for constitution with a suitable vehicle, for example, a sterile, pyrogen-free, water-based solution, before use.

For transmucosal administration, penetrants appropriate to the barrier to be permeated are used in the formulation. Such penetrants are generally known in the art.

For buccal administration, the compositions may take the form of tablets or lozenges formulated in conventional manner.

For administration by inhalation route, the active ingredients are conveniently delivered in the form of an aerosol spray presentation from a pressurized pack or a nebulizer with the use of a suitable propellant, for example, dichlorodifluoromethane, trichlorofluoromethane, dichloro-tetrafluoroethane, or carbon dioxide. In the case of a pressurized aerosol, the dosage may be determined by providing a valve to deliver a metered amount. Capsules and cartridges of, for example, gelatin for use in a dispenser may be formulated containing a powder mix of the compound and a suitable powder base, such as lactose or starch.

In some embodiments, the compositions of the present invention are formulated for rectal administration, for example, as suppositories or retention enemas, using, for example, conventional suppository bases such as cocoa butter or other glycerides.

The exact formulation, route of administration, and dosage can be chosen by the individual physician in view of the patient's condition.

In some embodiments, the composition further comprises at least one additive useful in the pharmaceutical fields, including, but not limited to fats, emulsifiers and co-emulsifiers, hydrophilic or lipophilic gelling agents, colorants, fragrances, emollients, humectants, preservatives, vitamins, chelators, solvents, fillers, thickeners, hydrophilic and lipophilic filters, dyestuffs, neutralizers, penetration-enhancing agents and polymers.

Non-limiting examples of suitable fats include mineral oils, oils of animal origin (lanolin), synthetic oils (isopropyl myristate, octyldodecyl, isostearyl isostearate, decyl oleate or isopropyl palmitate), silicone oils (cyclomethicone or dimethicone) and fluorinated oils. Fatty alcohol, fatty acids, waxes and gums, notably silicone gums and elastomers can also be used as fats.

Non-limiting examples of suitable emulsifiers and co-emulsifiers include polyglycerol fatty acid esters, sucrose fatty acid esters, sorbitane fatty acid esters, oxyethylene sorbitan fatty acid esters, PEG fatty alcohol ethers, glycerol fatty acid esters, alkyl sulphates, alkyl ether sulphates, alkyl phosphates, alkyl polyglucosides and dimethicone copolyols.

Non-limiting examples of suitable hydrophilic gelling include carboxyvinyl polymers (carbomer), acrylic copolymers such as acrylate/alkylacrylate copolymers, polyacrylamids, polysaccharides such as xanthan gum, guar gum, natural gums such as cellulose gum and derivatives, clays and 2-acrylamido-2-methylpropane acid copolymers.

Non-limiting examples of suitable lipophilic gelling agents include modified clays such as bentones, fatty acid metal salts, hydrophobic silica and ethylcellulose.

Non-limiting examples of suitable fillers include talc, kaolin, mica, serecite, magnesium carbonate, aluminum silicate and organic powders such as nylon.

Non-limiting examples of suitable dyestuffs include lipophilic dyes, hydrophilic dyes, pigments and mother-of-pearl commonly used in dermatological compositions, and their mixtures.

Non-limiting examples of suitable neutralizers include soda, triethanolamine, aminomethyl propanol and potassium hydroxide.

Non-limiting examples of suitable penetration enhancing agents include alcohols and glycols (ethanol and propylene glycol), ethoxydiglycol, alcohols and fatty acids (oleic acid), fatty acid esters and dimethyl isosorbide.

Non-limiting examples of preservatives compatible with pharmaceutical compositions include benzoic acid, its salts and esters, sorbic acid and its salts, parabens and their salts, triclosan, imidazolidinyl urea, phenoxyethanol, DMDM hydantoin, diazolidinyl urea and chlorphenesin.

Conventionally, the filters are UVA and UVB filters. Non-limiting examples of suitable UVA and UVB filters include organic filters such as benzophenone-3, butyl methoxydibenzoyl methane, octocrylene, octyl methoxycinnamate, 4-methylbenzylidene camphor, octyl salicylate, terephthalylidene dicamphor sulfonic acid and drometrizole trisiloxane, and non-organic filters such as titanium oxide and zinc oxide.

Non-limiting examples of suitable solvents include water, ethanol, glycerin, propylene glycol, butylene glycol and sorbitol.

The quantities of these various additives are those conventionally used in pharmaceutical preparations as is known to a person skilled in the art.

Methods and Uses of the Present Invention

According to one aspect of the present invention, there is provided a method for inducing an increase of the level of carnitine (L-carnitine, chemical name (3-hydroxy-4-N-trimethylamino-butyrate)) in skeletal muscle cells of a subject compared to baseline level.

In some embodiments, the method comprises administering to the subject a composition comprising as an active ingredient a peptide or a salt thereof having the amino acid sequence Cys-Lys-Met-Cys (SEQ ID NO: 1), for increasing of the level of carnitine in skeletal muscles cells of the a subject even above normal level.

According to another aspect of the present invention, there is provided a method for treating a disease or disorder affecting skeletal muscle tissue in a subject in need thereof, the method comprising administering to the subject a pharmaceutical composition comprising as an active ingredient a peptide or a salt thereof having the amino acid sequence Cys-Lys-Met-Cys (SEQ ID NO: 1) for treating or preventing the disease or disorder affecting skeletal muscle tissue in a subject.

The subject according to embodiments of the present invention is a mammal, typically a human.

In some embodiments, vitamin C is also administered, either within the same composition of the peptide or in a separate composition.

Vitamin C and the peptide may be administered concurrently. Vitamin C and the peptide may be administered sequentially. Vitamin C may be administered before or after the peptide. Vitamin C and the peptide may be administered using the same administration route. Vitamin C and the peptide may be administered using two different administration routes.

In some embodiments, L-carnitine is administered with the peptide, either within the same composition of the peptide or in a separate composition.

Carnitine and the peptide may be administered concurrently. Carnitine and the peptide may be administered sequentially. Carnitine may be administered before or after the peptide. Carnitine and the peptide may be administered using the same administration route. Carnitine and the peptide may be administered using two different administration routes.

An increase in the level of carnitine molecules in a tissue may be measured as compared to the level prior to administration. As used herein, "level" may refer to absolute quantity or concentration/percentage. Carnitine levels may be evaluated several hours after administration, but preferably after several days, during which the treated subject received more than one dose of the peptide/s and optionally vitamin C and/or carnitine.

In some embodiments, the increase in the level of carnitine molecules is an increase of more than about 50%, for example more than 60%, more than 70%, more than 80%, more than 90%, more than 100%, more than 120%, more than 150%. In some embodiments, the increase in the level of carnitine molecules is in the range of about 50%-200%, for example about 50%-100%, about 50%-150%.

In some embodiments, the peptides utilized herein increase carnitine levels in skeletal muscles without adversely affecting other organs, such as the kidneys.

Carnitine levels may be measured in a muscle sample, for example muscle biopsy, using methods known in the art, a non-limiting example being measurement using commercially available kits, such as the kit exemplified herein below. Carnitine levels may also be measured using magnetic resonance spectroscopy.

In some embodiments, administration of the compositions improves muscle energy metabolism. In some embodiments, administration of the compositions induces muscle hypertrophy. In some embodiments, administration of the compositions improves muscle strength. In some embodiments, administration of the compositions reduces muscle fatigue. In some embodiments, administration of the compositions improves endurance during physical activity.

In some embodiment, the compositions are administered to healthy subjects.

In some embodiments, the disease or disorder is carnitine deficiency. Carnitine deficiency is a metabolic state in which carnitine concentrations in plasma and/or tissues are less than the levels required for normal function of the organism or of that specific tissue. It may be primary or secondary. It may be systemic or muscle-restricted. It may be inherited or acquired.

Primary carnitine deficiency may be caused by a deficiency in the plasma membrane carnitine transporter, with urinary carnitine wasting causing systemic carnitine depletion. Intracellular carnitine deficiency impairs the entry of long-chain fatty acids into the mitochondrial matrix. Consequently, long-chain fatty acids are not available for beta-oxidation and energy production, and the production of ketone bodies is also impaired. Primary carnitine deficiency is characterized, inter alia, by myopathy.

Secondary carnitine deficiency is caused by other metabolic disorders (e.g. fatty acid oxidation disorders). Secondary carnitine deficiency may be caused, for example, by increased losses, pharmacological therapy, a number of inherited metabolic disorders, poor diet or malabsorption of carnitine.

Muscle carnitine deficiency (restricted to muscle) is characterized by depletion of carnitine levels in muscle with normal serum concentrations. Evidence indicates that the causal factor is a defect in the muscle carnitine transporter.

The different types of carnitine deficiencies are reviewed, for example, in Flanagan et al. *Nutrition & Metabolism* 2010, 7:30.

In some embodiments, the disease or disorder is primary carnitine deficiency. In additional embodiments, the disease or disorder is secondary carnitine deficiency. In some embodiments, the carnitine deficiency is systemic. In additional embodiments, the carnitine deficiency is muscle-restricted.

In some embodiments, the disease or disorder is a mitochondrial myopathy. Mitochondrial myopathies are a group of neuromuscular diseases caused by damage to the mitochondria. Types of mitochondrial myopathies are reviewed, for example, in "Facts About Mitochondrial Myopathies" by Muscular dystrophy association (MDA) Inc., December 2009.

In some embodiments, the mitochondrial myopathy is selected from the group consisting of Kearns-Sayre syndrome, myoclonus epilepsy with ragged red fibers (MERRF), mitochondrial encephalomyopathy, lactic acidosis and stroke-like episodes (MELAS), Leigh syndrome, mitochondrial DNA depletion syndrome (MDS), neuropathy, ataxia and retinitis pigmentosa (NARP) and Pearson syndrome. Each possibility represents a separate embodiment of the invention.

In some embodiments, the disease or disorder is a metabolic myopathy. Metabolic myopathies are a group of hereditary muscle disorders caused by specific enzymatic defects due to defective genes. Metabolic myopathies are heterogeneous conditions that have common abnormalities of muscle energy metabolism that result in skeletal muscle dysfunction. Information about the different types of metabolic myopathies can be found, for example, in the Merck Manual, currently available online at: www.merckmanuals.com/professional/index.html.

In some embodiments, the metabolic myopathy is a lipid storage disease.

In some embodiments, the lipid storage disease is selected from the group consisting of carnitine palmitoyltransferase (CPT) deficiency (including both CPT I and CPT II), carnitine/acylcarnitine translocase deficiency, very long-chain acylCoA dehydrogenase (VLCAD) deficiency, long-chain 3-hydroxyacyl-CoA dehydrogenase (LCHAD) deficiency, mitochondrial trifunctional protein (TFP) deficiency, medium-chain acylCoA dehydrogenase (MCAD) deficiency and glutaric aciduria type II. Each possibility represents a separate embodiment of the invention.

In some embodiments, the disease or disorder is a neuromuscular disease. Neuromuscular diseases are a group of diseases that either directly, via intrinsic muscle pathology, or indirectly, via nerve pathology or neuromuscular junction pathologies, impair the functioning of the muscles.

In some embodiments, the neuromuscular disease is selected from the group consisting of muscular dystrophy (including Becker muscular dystrophy, Duchenne muscular dystrophy, Emery-Dreifuss muscular dystrophy, Facioscapulohumeral muscular dystrophy, Limb-girdle muscular dystrophy, myotonia congenita and myotonic dystrophy), myasthenia gravis and amyotrophic lateral sclerosis (ALS). Each possibility represents a separate embodiment of the invention.

The method of the present invention may be combined with one or more known treatments of the above described disorders.

In some embodiments, the present invention provides the use of at least one peptide of the present invention or a salt thereof, and optionally vitamin C or a salt thereof, for the manufacture of a medicament for the treatment of a disease or disorder affecting muscle tissue.

The present invention further provides a kit for treating a disease or disorder affecting a muscle tissue, the kit comprises a composition comprising at least one peptide of the present invention or a salt thereof, and optionally vitamin C or a salt thereof, and instructions for administering said composition to a subject in need thereof.

In some embodiments, the kit comprises a composition comprising at least one peptide or a salt thereof, and a composition comprising vitamin C or a salt thereof.

In some embodiment, the kit comprises means for administering the composition or compositions. For example, the kit may include a syringe.

The amount of the composition of the present invention to be administered for the above indications, the administration regimes as well as their mode of application will depend both on characteristics of the treated individual (age, size, gender, etc.) as well as on parameters associated with the phenomena to be treated.

The following examples are presented in order to more fully illustrate certain embodiments of the present invention. They should in no way, however, be construed as limiting the broad scope of the invention. One skilled in the art can readily devise many variations and modifications of the principles disclosed herein without departing from the scope of the invention.

EXAMPLES

Example 1

Effect of N-acetyl-Cys-Lys-Met-Cys-$NH_2$ (SEQ ID NO: 3) on Carnitine Levels in Mouse Tissues The peptide N-acetyl-Cys-Lys-Met-Cys-$NH_2$, designated herein as "DY-65" (SEQ ID NO: 3) was synthesized by Solid Phase Peptide Synthesis (SPSS) using Fmoc strategy (>98% pure), as disclosed in WO 2012/098546.

The peptide was prepared by SPSS in which there were repeated cycles of coupling and deprotection. The first stage of the technique consisted of peptide chain assembly with protected amino acid derivatives on a polymeric support. The second stage of the technique was the cleavage of the peptide from the resin support with the concurrent cleavage of all side chain protecting groups to give the crude free peptide.

The free N-terminal amine of a solid-phase attached peptide was first coupled to a single N-protected amino acid unit. This unit was then deprotected, revealing a new N-terminal amine to which a further amino acid was attached. After cleavage from the resin, peptides were then purified by reverse phase HPLC using columns.

Fmoc Deprotection:

0.08 mmol of Fmoc-X-Wang resin was loaded into a fitted column equipped with a plastic cap. The resin was washed twice with 3 mL portions of dimethylformamide (DMF) for 1 minute each. Next, 3 ml of 20% piperidine in DMF was added and deprotection allowed to continue for 15 minutes. During this time, the column was gently swirled in order to assure a complete mixing. After the reaction was complete (in about 15 minutes), the reaction column was drained and the resin washed 4 times with 3 mL of DMF.

Amide Bond Coupling:

In a small vial, 3 equivalents of the Fmoc amino acid was preactivated by combining it with equal equivalents of O-Benzotriazole-N,N,N',N'-tetramethyl-uronium-hexafluoro-phosphate (HBTU), 6 equivalents of DIPEA (N,N'-diisopropylethylamine), and 3 mL of DMF. This solution was fully dissolved and then allowed to react for an additional 3-5 minutes. Then this coupling solution was added to the resin. The cap was placed on the reaction column and the resin slurry agitated every 2-3 minutes over a period of 20 minutes.

Cleavage:

In order to obtain the peptide in the free acid form, the ester linkage was cleaved using trifluoroacetic acid (TFA). The resin was treated with 2-3 mL of a solution of TFA and water in a ratio of 95:5. The resin was then agitated over a period of 25 minutes. The column was subsequently drained and the filtrated collected into a glass collection vessel. The material was then dried in diethyl ether and analyzed.

The Peptide was Tested as Follows:

Male ICR mice were injected i.p. with 250 mg/kg of the DY-65 peptide for 5 consecutive days. Half an hour after the last injection lung, heart, skeletal muscle (femural), brain, liver, kidney and blood were removed, homogenized (100 mg tissue in 200 μl distilled water), centrifuged and filtrated through 30K Microcon® filter. Carnitine analysis was carried out by a commercial kit (BIOVISION™, catalogue number K642-100). n=4 for each group.

The results have shown a remarkable and specific elevation of about 150% in the level of carnitine in skeletal muscle tissue of healthy animals that were treated with the DY-65 peptide ($p<0.05$) (FIG. 1). Advantageously, no toxicity effects were observed despite the high dose of the peptide that was used. Surprisingly, other tissues, including liver and kidneys which are normally the main sites of L-carnitine biosynthesis, did not demonstrate a significant elevation in carnitine level after treatment with the DY-65 peptide. The results were verified in pooled tissues, as well as in individual animals.

Example 2

Comparative-Effect of N-Acetyl-Cys-Met-Lys-Cys-$NH_2$ (SEQ ID NO: 4) on Carnitine Levels in Mouse Tissues The experiment described in Example 1 was repeated, this time with the peptide N-acetyl-Cys-Met-Lys-Cys-$NH_2$ designated herein as "DY-70" (SEQ ID NO: 4). Administration of DY-70 did not result in increased carnitine levels compared to baseline levels in any of the tissues that were examined.

Example 3

Effect of Peptide Administration Versus Direct Carnitine Administration

The experiment described in Example 1 is repeated, this time in comparison to administration of carnitine molecules.

Example 4

Effect of Peptide in Combination with Vitamin C

The experiment described in Example 1 is repeated, this time in comparison to administration of DY-65 and vitamin C.

Example 5

Effect of Peptide in Combination with L-Carnitine

The experiment described in Example 1 is repeated, this time in comparison to administration of DY-65 and L-carnitine.

The foregoing description of the specific embodiments will so fully reveal the general nature of the invention that others can, by applying current knowledge, readily modify and/or adapt for various applications such specific embodiments without undue experimentation and without departing from the generic concept, and therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed chemical structures and functions may take a variety of alternative forms without departing from the invention.

The invention claimed is:

1. A method for increasing the level of carnitine in skeletal muscle tissues, the method comprising administering a composition comprising a peptide or a salt thereof as an active ingredient having the amino acid sequence Cys-Lys-Met-Cys (SEQ ID NO: 1) to a subject in need of an increase of carnitine levels in skeletal muscle tissues.

2. The method of claim 1, wherein the peptide has 4-10 amino acids.

3. The method of claim 1, wherein the composition is selected from the group consisting of a pharmaceutical composition, a dietary supplement and a medical food.

4. The method of claim 1, wherein the peptide further comprises at least one modification selected from the group consisting of an amino-terminal modification and a carboxy terminal modification.

5. The method of claim 4, wherein the amino terminal modification is an amino terminal blocking group.

6. The method of claim 5, wherein the amino-terminal blocking group is an alkyl group or an acyl group.

7. The method of claim 4, wherein the amino-terminal blocking group is an acetyl group.

8. The method of claim 4, wherein the amino terminal modification is a permeability-enhancing moiety selected from the group consisting of lipids, fatty acids, steroids and bulky aromatic and aliphatic compounds.

9. The method of claim 4, wherein the carboxy terminal modification is a carboxy terminal blocking group.

10. The method of claim 9, wherein the carboxy terminal blocking group is selected from the group consisting of an amide, ester and alcohol.

11. The method of claim 9, wherein the carboxy terminal blocking group is an amide.

12. The method of claim 1, wherein the composition further comprises vitamin C or a salt thereof or L-carnitine or a salt thereof as an additional active ingredient.

13. The method of claim 1, further comprising administering vitamin C or a salt thereof or L-carnitine or a salt thereof as an additional active ingredient.

14. The method of claim 1, wherein the peptide is a tetra-peptide.

15. The method of claim 14, wherein the peptide is N-acetyl-Cys-Lys-Met-Cys-$NH_2$ (SEQ ID NO: 3).

16. The method of claim 1, wherein the subject is having a disease or disorder affecting skeletal muscle tissues selected from the group consisting of carnitine deficiency, a mitochondrial myopathy, a metabolic myopathy and a neuromuscular disease.

* * * * *

UNITED STATES PATENT AND TRADEMARK OFFICE
CERTIFICATE OF CORRECTION

Page 1 of 1

PATENT NO. : 9,499,582 B2
APPLICATION NO. : 14/603792
DATED : November 22, 2016
INVENTOR(S) : Josef Mograbi It is certified that error appears in the above-identified patent and that said Letters Patent is hereby corrected as shown below:

On the Title Page

Change Item (73) Assignee:

from
"GENESISTEC LTD., Katzrin (IL)"

to
-- ONEDAY - BIOTECH AND PHARMA LTD., Tel Aviv (IL) --

Signed and Sealed this
Eighteenth Day of April, 2017

Michelle K. Lee
*Director of the United States Patent and Trademark Office*

```
                              SEQUENCE LISTING

<160> NUMBER OF SEQ ID NOS: 5

<210> SEQ ID NO 1
<211> LENGTH: 4
<212> TYPE: PRT
<213> ORGANISM: Artificial Sequence
<220> FEATURE:
<223> OTHER INFORMATION: Peptide

<400> SEQUENCE: 1

Cys Lys Met Cys
1

<210> SEQ ID NO 2
<211> LENGTH: 4
<212> TYPE: PRT
<213> ORGANISM: Artificial Sequence
<220> FEATURE:
<223> OTHER INFORMATION: Peptide

<400> SEQUENCE: 2

Cys Met Lys Cys
1

<210> SEQ ID NO 3
<211> LENGTH: 4
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: N-terminal acetyl group
<220> FEATURE:
<221> NAME/KEY: MISC_FEATURE
<222> LOCATION: (4)..(4)
<223> OTHER INFORMATION: C-terminal amide group

<400> SEQUENCE: 3

Cys Lys Met Cys
1

<210> SEQ ID NO 4
<211> LENGTH: 4
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: N-terminal acetyl group
```

```
<220> FEATURE:
<221> NAME/KEY: MISC_FEATURE
<222> LOCATION: (4)..(4)
<223> OTHER INFORMATION: C-terminal amide group

<400> SEQUENCE: 4

Cys Met Lys Cys
1

<210> SEQ ID NO 5
<211> LENGTH: 4
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: Optional N-terminal modification
<220> FEATURE:
<221> NAME/KEY: MISC_FEATURE
<222> LOCATION: (4)..(4)
<223> OTHER INFORMATION: Optional C-terminal modification

<400> SEQUENCE: 5

Cys Lys Met Cys
1
```